(12) United States Patent
Jayagopal et al.

(10) Patent No.: US 10,076,578 B2
(45) Date of Patent: Sep. 18, 2018

(54) PROBES FOR IMAGING OF HYPOXIA

(71) Applicant: Vanderbilt University, Nashville, TN (US)

(72) Inventors: Ashwath Jayagopal, Nashville, TN (US); Kwangho Kim, Nashville, TN (US); Gary Sulikowski, Brentwood, TN (US); Stephanie Evans, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 317 days.

(21) Appl. No.: 14/871,866

(22) Filed: Sep. 30, 2015

(65) Prior Publication Data
US 2016/0151517 A1 Jun. 2, 2016

Related U.S. Application Data

(60) Provisional application No. 62/058,643, filed on Oct. 1, 2014.

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *C07D 493/10* | (2006.01) | |
| *G01N 33/58* | (2006.01) | |
| *G01N 33/533* | (2006.01) | |

(52) U.S. Cl.
CPC ...... *A61K 49/0052* (2013.01); *A61K 49/0041* (2013.01); *C07D 493/10* (2013.01); *G01N 33/533* (2013.01); *G01N 33/582* (2013.01); *A61K 49/0043* (2013.01); *G01N 2800/52* (2013.01); *G01N 2800/7038* (2013.01)

(58) Field of Classification Search
None
See application file for complete search history.

(56) References Cited

U.S. PATENT DOCUMENTS

2008/0102026 A1* 5/2008 Lee .................... A61K 41/0095
424/1.11

FOREIGN PATENT DOCUMENTS

JP 2010203966 9/2010

OTHER PUBLICATIONS

Okuda et al. (Bioconj. Chem. 2012, 23, 324-329).*
Okuda, et al., 2-Nitroimidazole-Tricarbocyanine Conjugate as a Near-Infrared Fluorescent Probe for in Vivo Imaging of Tumor Hypoxia; Bioconjugate Chem. 2012, 23; pp. 324-329.
Bergeron, et al., Detection of Hypoxic Cells With the 2-Nitroimidazole, Ef5, Correlates With Early Redox Changes in Rat Brain After Perinatal Hypoxia-Ischemia; Neuroscience; 1999; vol. 89, No. 4, pp. 1357-1366.
Zha, et al., Synthesis and evaluation of two novel 2-nitroimidazole derivatives as potential PET radioligands for tumor imaging; Nucl Med Biol. May 2011 ; 38(4): 501-508.
Linsenmeier, R. A., Braun, R. D., McRipley, M. A., Padnick, L. B., Ahmed, J., Hatchell, D. L., McLeod, D. S., and Lutty, G. A. (1998) Retinal hypoxia in long-term diabetic cats. Investigative ophthalmology & visual science 39, 1647-57.
Traustason, S., Kiilgaard, J. F., Karlsson, R. A., Hardarson, S. H., Stefansson, E., and Ia Cour, M. (2013) Spectrophotometric retinal oximetry in pigs. Investigate opthalmology & visual science 54, 2746-51.
Hardarson, S. H., Elfarsson, A., Agnarsson, B. A., and Stefansson, E. (2013) Retinal oximetry in central retinal artery occlusion. Acta ophthalmologica 91, 189-90.
Hammer, M., Vilser, W., Riemer, T., and Schweitzer, D. (2008) Retinal vessel oximetry-calibration, compensation for vessel diameter and fundus pigmentation, and reproducibility. Journal of biomedical optics 13, 054015.
Hardarson, S. H., Harris, A., Karlsson, R. A., Halldorsson, G. H., Kagemann, L., Rechtman, E., Zoega, G. M., Eysteinsson, T., Benediktsson, J. A., Thorsteinsson, A., Jensen, P. K., Beach, J., and Stefansson, E. (2006) Automatic retinal oximetry. Investigative ophthalmology & visual science 47, 5011-6.
Kristjansdottir, J. V., Hardarson, S. H., Harvey, A. R., Olafsdottir, O. B., Eliasdottir, T. S., and Stefansson, E. (2013) Choroidal oximetry with a noninvasive spectrophotometric oximeter. Investigative ophthalmology & visual science 54, 3234-9.
(Continued)

*Primary Examiner* — Michael G Hartley
*Assistant Examiner* — Melissa J Perreira
(74) *Attorney, Agent, or Firm* — Stites & Harbison PLLC; Mandy Wilson Decker

(57) ABSTRACT

Exemplary probes for detecting hypoxic cells and tissue have the structure of

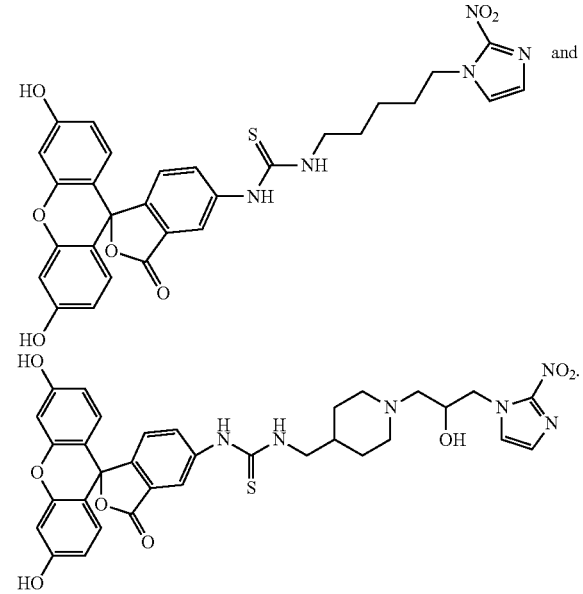

15 Claims, 12 Drawing Sheets

(56) References Cited

OTHER PUBLICATIONS

Wanek, J., Teng, P. Y., Blair, N. P., and Shahidi, M. (2013) Inner retinal oxygen delivery and metabolism under normoxia and hypoxia in rat. Investigate opthalmology & visual science 54, 5012-9.

Ljungkvist, A. S., Bussink, J., Rijken, P. F., Raleigh, J. A., Denekamp, J., and Van Der Kogel, A. J. (2000) Changes in tumor hypoxia measured with a double hypoxic marker technique. Int J Radiat Oncol Biol Phys 48, 1529-38.

Varia, M. A., Calkins-Adams, D. P., Rinker, L. H., Kennedy, A. S., Novotny, D. B., Fowler, W. C., Jr., and Raleigh, J. A. (1998) Pimonidazole: a novel hypoxia marker for complementary study of tumor hypoxia and cell proliferation in cervical carcinoma. Gynecologic oncology 71, 270-7.

Arteel, G. E., Thurman, R. G., and Raleigh, J. A. (1998) Reductive metabolism of the hypoxia marker pimonidazole is regulated by oxygen tension independent of the pyridine nucleotide redox state. European journal of biochemistry / FEBS 253, 743-50.

Nordsmark, M., Loncaster, J., Aquino-Parsons, C., Chou, S. C., Ladekarl, M., Havsteen, H., Lindegaard, J. C., Davidson, S. E., Varia, M., West, C., Hunter, R., Overgaard, J., and Raleigh, J. A. (2003) Measurements of hypoxia using pimonidazole and polarographic oxygen-sensitive electrodes in human cervix carcinomas. Radiotherapy and oncology : journal of the European Society for Therapeutic Radiology and Oncology 67, 35-44.

Yaromina, A., Zips, D., Thames, H. D., Eicheler, W., Krause, M., Rosner, A., Haase, M., Petersen, C., Raleigh, J. A., Quennet, V., Walenta, S., Mueller-Klieser, W., and Baumann, M. (2006) Pimonidazole labelling and response to fractionated irradiation of five human squamous cell carcinoma (hSCC) lines in nude mice: the need for a multivariate approach in biomarker studies. Radiotherapy and oncology : journal of the European Society for Therapeutic Radiology and Oncology 81, 122-9.

Nordsmark, M., Loncaster, J., Chou, S. C., Haysteen, H., Lindegaard, J. C., Davidson, S. E., Varia, M., West, C., Hunter, R., Overgaard, J., and Raleigh, J. A. (2001) Invasive oxygen measurements and pimonidazole labeling in human cervix carcinoma. International journal of radiation oncology, biology, physics 49, 581-6.

Piao, W., Tsuda, S., Tanaka, Y., Maeda, S., Liu, F., Takahashi, S., Kushida, Y., Komatsu, T., Ueno, T., Terai, T., Nakazawa, T., Uchiyama, M., Morokuma, K., Nagano, T., and Hanaoka, K. (2013) Development of azo-based fluorescent probes to detect different levels of hypoxia. Angewandte Chemie 52, 13028-32.

Kiyose, K., Hanaoka, K., Oushiki, D., Nakamura, T., Kajimura, M., Suematsu, M., Nishimatsu, H., Yamane, T., Terai, T., Hirata, Y., and Nagano, T. (2010) Hypoxia-sensitive fluorescent probes for in vivo real-time fluorescence imaging of acute ischemia. Journal of the American Chemical Society 132, 15846-8.

Takahashi, S., Piao, W., Matsumura, Y., Komatsu, T., Ueno, T., Terai, T., Kamachi, T., Kohno, M., Nagano, T., and Hanaoka, K. (2012) Reversible off-on fluorescence probe for hypoxia and imaging of hypoxia-normoxia cycles in live cells. Journal of the American Chemical Society 134, 19588-91.

\* cited by examiner

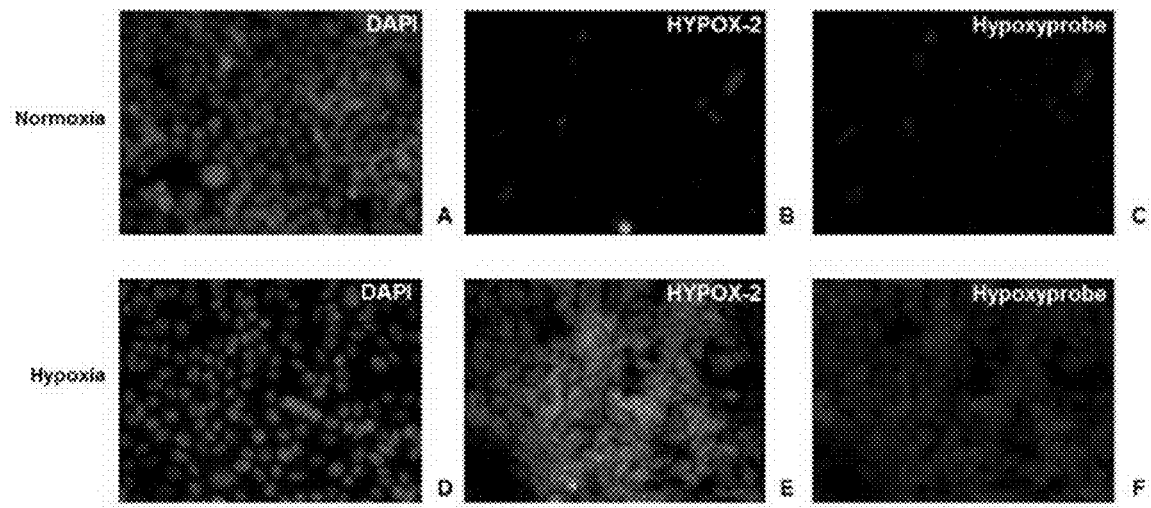
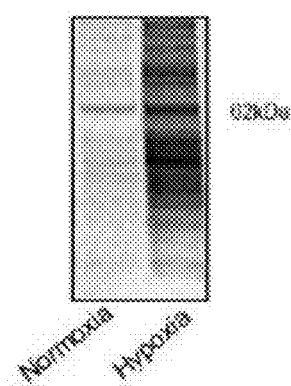
FIG. 2A-2F
FIG. 2G

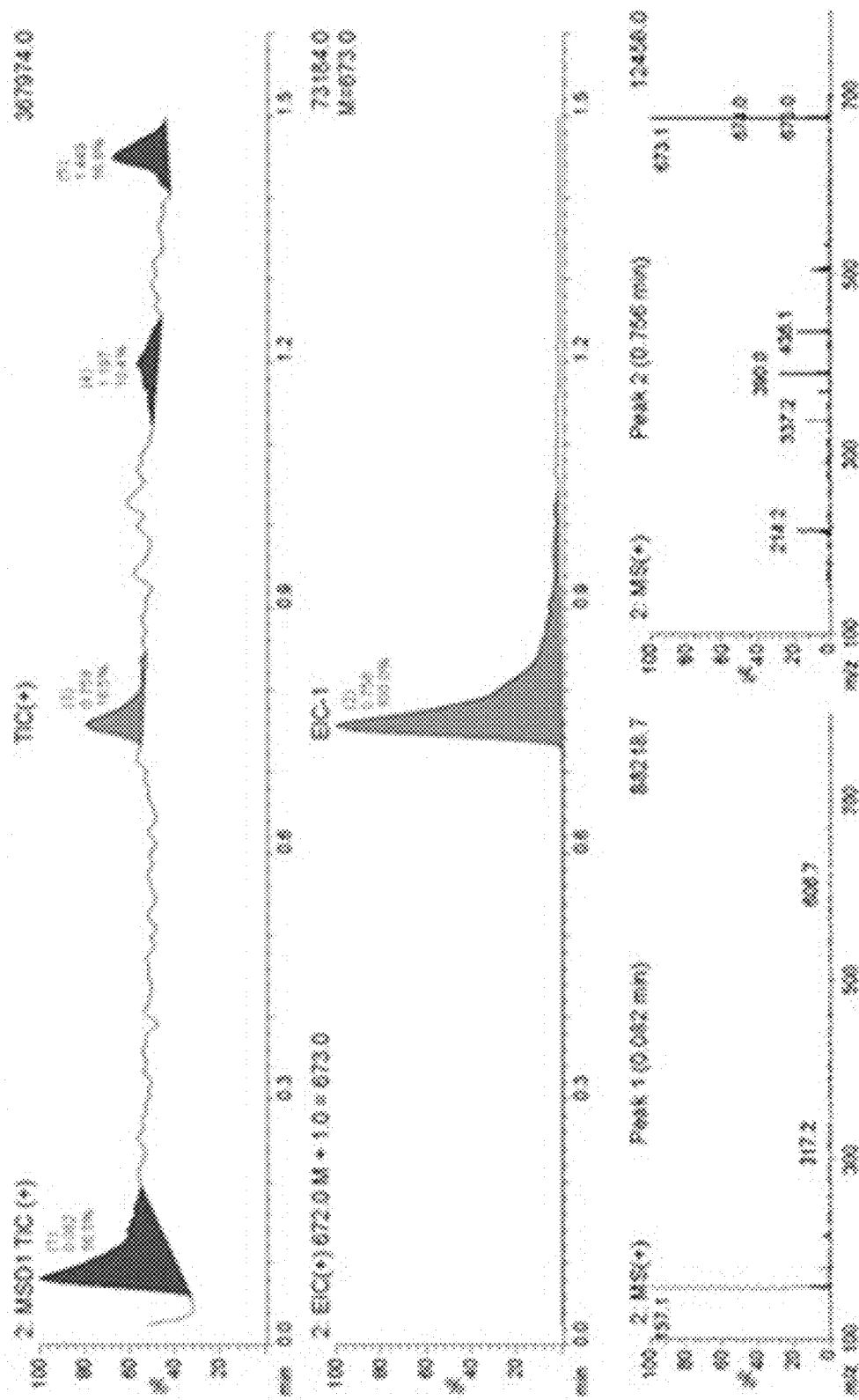
FIG. 8, Cont'd

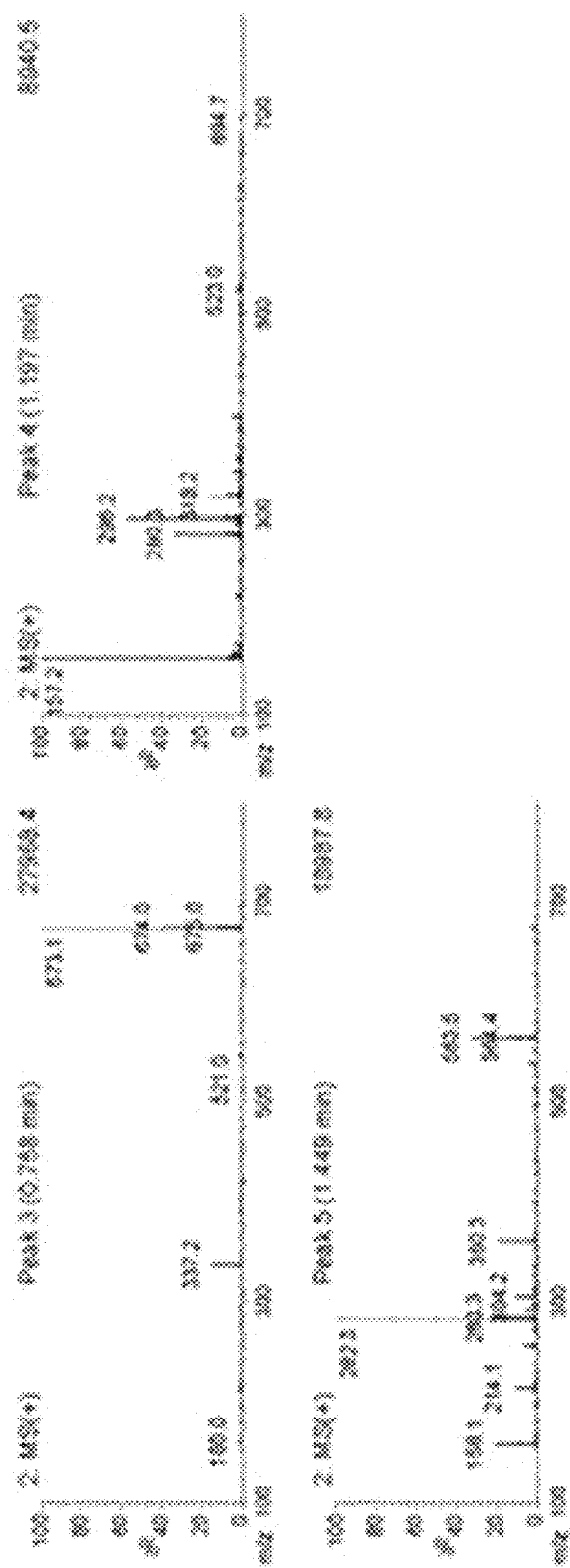
FIG. 8, Cont'd

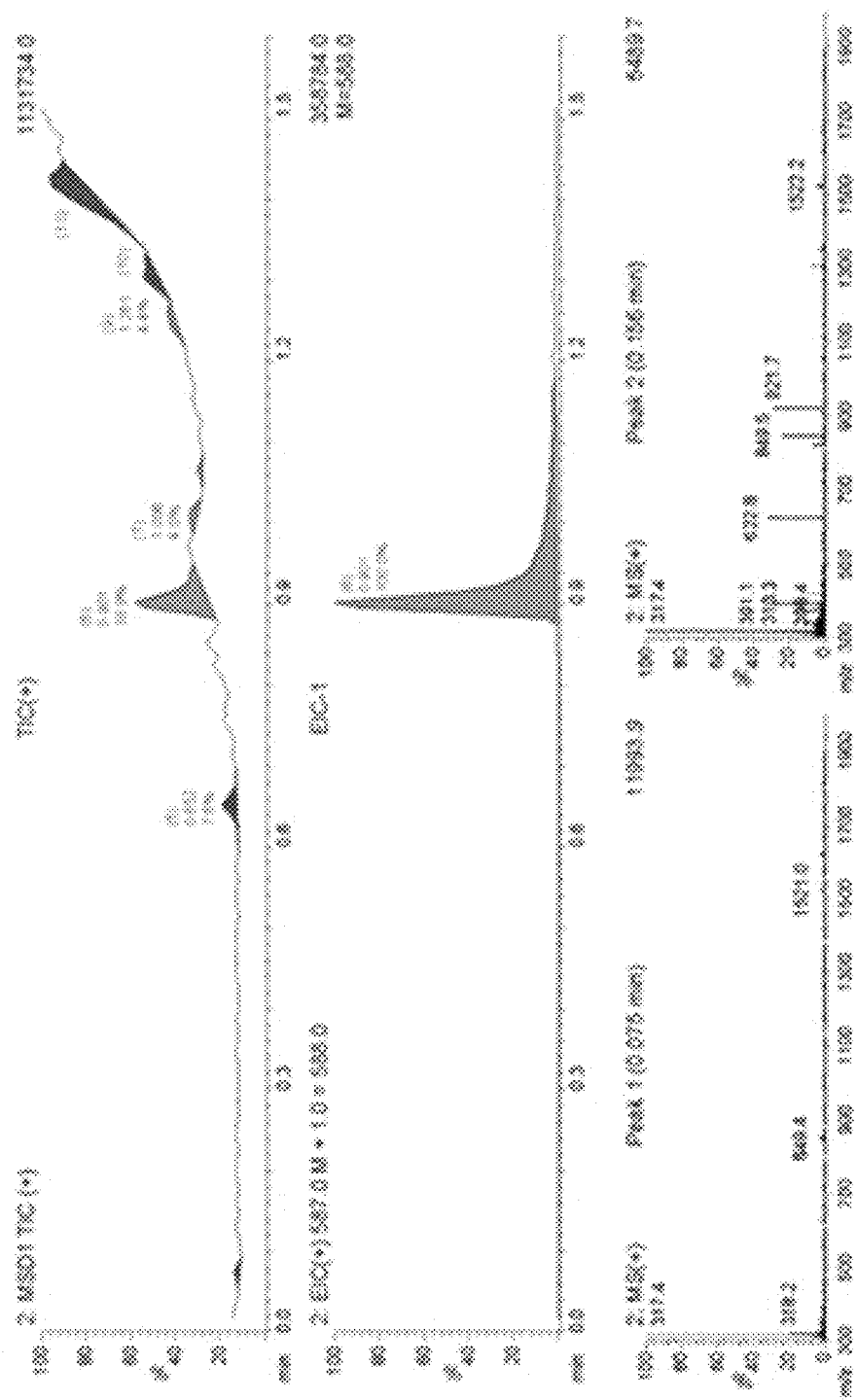
FIG. 10, Cont'd

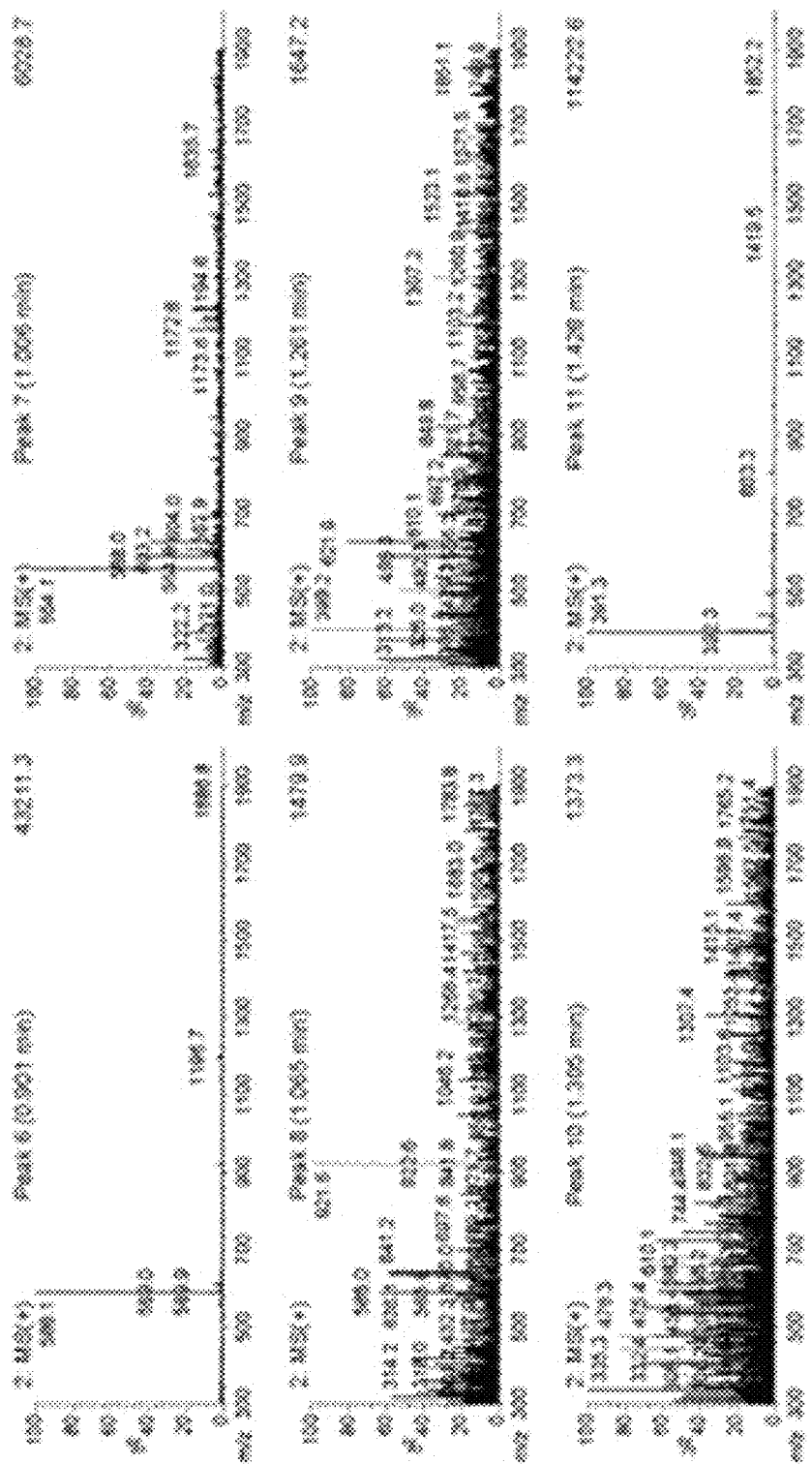
FIG. 10, Cont'd

PROBES FOR IMAGING OF HYPOXIA

RELATED APPLICATIONS

This application claims priority from U.S. Provisional Application Ser. No. 62/058,643 filed Oct. 1, 2014, the entire disclosure of which is incorporated herein by this reference.

GOVERNMENT INTEREST

This invention was made with government support under grant number EY023397 awarded by the National Institutes of Health. The government has certain rights in the invention.

TECHNICAL FIELD

The presently-disclosed subject matter generally relates to probes for imaging hypoxia. In particular, certain embodiments of the presently-disclosed subject matter relate to probes for imaging hypoxia in the retina in vivo.

BACKGROUND

The retina is supplied with oxygen by two separate vascular systems, the choroidal or outer retinal circulation, and the inner retinal circulation (1). Adequate oxygen supply is critical for normal functioning of the retina. The high oxygen requirements of the retina for proper function and the unique structure required for light to reach the photoreceptors make it vulnerable to vascular diseases (2).

Hypoxia plays a role in the onset and progression of various retinal vascular diseases that can cause of irreversible vision loss, including diabetic retinopathy, retinopathy of prematurity, and age-related macular degeneration (3-5).

Advancements in technologies including retinal oximetry, phosphorescence lifetime imaging, and Doppler optical coherence tomography (OCT) have provided a greater understanding of vascular oxygen supply and metabolism in the retina. Retinal oximetry measures vascular oxygen tension in inner retinal (6-9) and choroidal vasculature (10) based on hemoglobin oxygen saturation. Phosphorescence lifetime imaging measures oxygen levels using an oxygen sensitive agent that is quenched by oxygen allowing for vascular $pO_2$ levels to be quantified (11). Doppler OCT measures retinal blood flow, which can be used to derive retinal oxygen metabolic measurements (12). However, known methods and systems are unable to detect retinal hypoxia in vivo. Instead, current methods and systems rely on dissection and immunostaining in order to identify hypoxia in the retina. This makes it difficult or impossible to achieve early disease detection, monitoring of disease progression, and assessment of therapeutic responses in the patient.

Accordingly, there remains a need for probes which enable visualization of hypoxic tissue in the retina and other tissues. Furthermore, there remains a need to develop such probes that can work to identify hypoxic cells in living tissue.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes hypoxia-sensitive probes and methods for making and using the same. In some embodiments the present probes are based on biocompatible nitroimidazole and fluorescein components. The present compounds are capable of detection of hypoxic tissues and cells with relatively high specificity and sensitivity. Additionally, embodiments of the present compounds are capable of detecting hypoxic tissue and cells in vivo.

In some embodiments, the nitroimidazole compound of the probe is selected from 2-nitroimidazole and pimonidazole. In some embodiments, the probe has the following structure, which is also referred to herein as HYPOX-1:

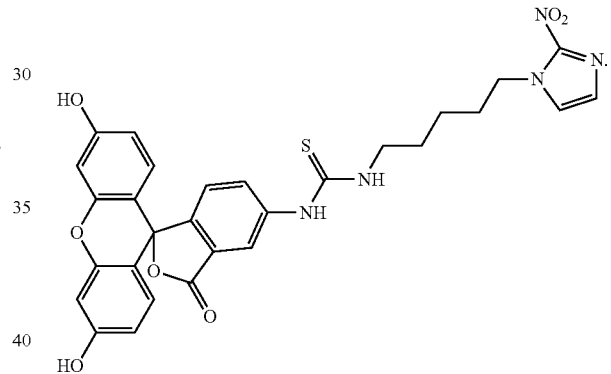

In some embodiments, the probe has the following structure, which is also referred to herein as HYPOX-2:

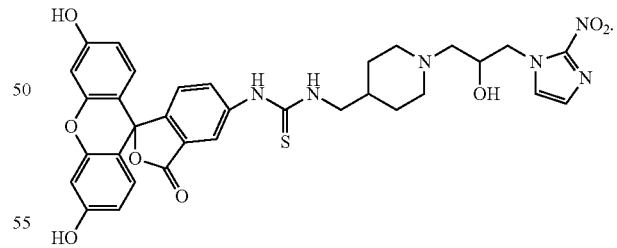

The presently-disclosed subject matter also includes methods for detecting hypoxic cells and tissue, which involve contacting the cells or tissue with a probe as disclosed herein; and detecting fluorescent intensity of the cell or tissue, wherein increased fluorescent intensity indicates that the cells or tissue is hypoxic. Embodiments of the probes disclosed acquire fluorescence as the nitro groups of the probe are bioreduced by nitroreductases in hypoxic cells or tissue. In this regard, increasing fluorescent intensity is indicative of hypoxia.

As will be recognized by those of ordinary skill in the art, the ability to image hypoxia in a variety of cells and tissue has particular advantages, including, for example, tumor cells or tissue, retinal cells or tissue, or other cells or tissue. By way of example, imaging tumor hypoxia can allow for better prognosis, for better determination of therapies for determining efficacy of certain treatments, e.g., radiation therapy, or for more effectively treating a cancer, e.g., identifying tumors or populations of cancerous cells that could be treated using anti-hypoxia therapies. For another example, imaging hypoxia associated with retinal cells can provide useful information about retinal disease.

Some embodiments of the methods disclosed herein involve administering the probe to living cells or tissue, or administering the probe in vivo. In this regard, where the cells or tissue include cancer or tumor cells, detecting fluorescent intensity can be used to determine whether the subject is likely to benefit from certain treatments and/or determining efficacy of certain treatments that have been administered. Where the cells or tissue includes retinal cells of a subject, detecting fluorescent intensity can be used to determine whether the subject is likely to have hypoxic cells or tissue, or is likely to have a retinal disease.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2A-2F. R28 retinal neuronal cell lines conditioned under normoxic or hypoxic (4 h) conditions were incubated with 100 μM HYPOX-2 followed by fixation and immunostaining with an antibody specific for pimonidazole adducts in hypoxic cells.

FIG. 2G. HYPOX-1 accumulation in hypoxic retinal cells occur through nitroimidazole adduct formation. Human Retinal Microvascular Endothelial Cells (HRMEC) were treated with 100 μM HYPOX-1 under normoxic or hypoxic conditions for 4 h. Cell lysates were probed with an anti-Hypoxyprobe antibody by Western analysis. Adduct formation was increased in hypoxic cells.

FIGS. 4(A) and 4(C) HYPOX-1 in P13 OIR mouse retina. FIGS. 4(B) and 4(D) Pimonidazole immunostaining colocalizes with HYPOX-1 region. FIG. 4(E) Room air mice exhibited no HYPOX-1 accumulation. FIG. 4(F) There was no pimonidazole accumulation as they exhibited minimal fluorescence when stained with Hypoxyprobe.

DESCRIPTION OF EXEMPLARY EMBODIMENTS

Figure 1A:
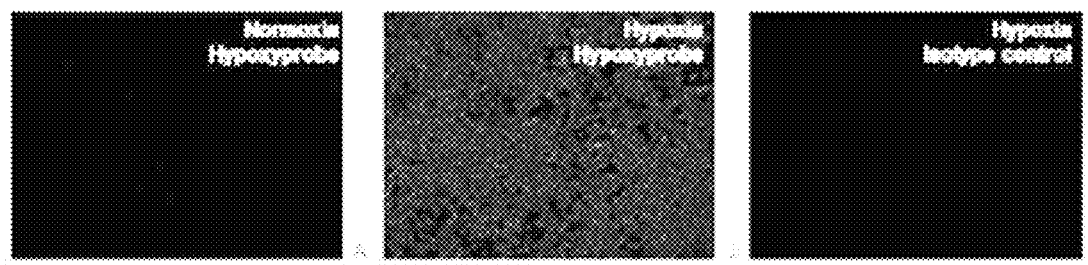
FIG. 1A. R28 cells were treated with 100 μM pimonidazole hydrochloride (Hypoxyprobe) and subjected to normoxia or hypoxia-conditioning for 4 h, followed by Hypoxyprobe adduct immunostaining. (Left Panel) Normoxia-conditioned cells exhibited minimal fluorescence. (Middle Panel) Hypoxia-conditioned cells exhibited positive staining for Hypoxiprobe. (Right Panel) Hypoxia-conditioned cells stained with an isotype control IgG exhibited no fluorescence.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Although any methods, devices, and materials similar or equivalent to those described herein can be used in the practice or testing of the presently-disclosed subject matter, representative methods, devices, and materials are now described.

The presently-disclosed subject matter includes hypoxia-sensitive probes and methods for making and using the same. In some embodiments the present probes are based on biocompatible nitroimidazole and fluorescein components. The present compounds are capable of detection of hypoxic tissues and cells with relatively high specificity and sensitivity. Additionally, embodiments of the present compounds are capable of detecting hypoxic tissue and cells in vivo.

As used herein, the term "probe" is used to refer to a compound or substance that can serve as an indicator of a particular condition. In some instances the probes can serve as an indicator by selectively targeting and/or binding a cell or tissue of interest, such as a hypoxic cell or tissue. Thus, a probe can refer to a compound or substance that can serve as an indicator of hypoxia. In this regard, the term probe can also be used interchangeably with the terms "imaging agent," "compounds," and the like herein.

The term "tissue" is used herein to refer to a population of cells, generally consisting of cells of the same kind that perform the same or similar functions. The types of cells that make the tissue are not limited. In some embodiments tissue is part of a living organism, and in some embodiments tissue is tissue excised from a living organism or artificial tissue. In some embodiments tissue can be part of a retina. In some embodiments tissue can be part of a tumor In some embodiments the present probes include a nitroimidazole compound selected from 2-nitroimidazole and pimonidazole. In some embodiments the probes include a nitroimidazole component and a fluorescein component. In some embodiments, the nitroimidazole compound of the probe is selected from 2-nitroimidazole and pimonidazole. In some embodiments the probes include fluorescein and pimonidazole. In other embodiments the probes include fluorescein and 2-nitroimidazole. Those of ordinary skill in the art upon reviewing the present disclosure will appreciate other fluorescent compounds and nitroimidazole compounds that can be utilized to synthesize a hypoxia-sensitive probe. The present inventors have thus conceived of probes that include a conjugation of fluorescing dyes to hypoxia-sensitive nitroimidazole moieties, such as 2-nitroimidazole and pimonidazole, which are known to accumulate within hypoxic cells (13-15).

In some embodiments, the probe has the following structure, which is also referred to herein as HYPOX-1:

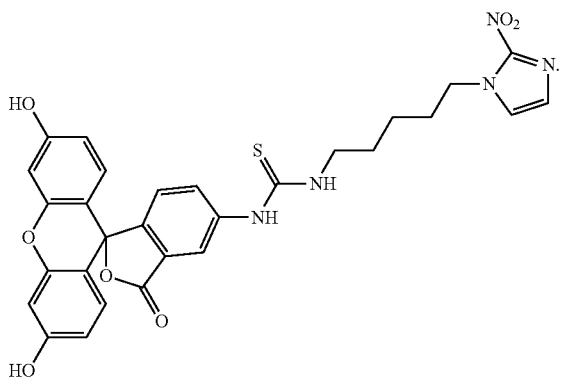 [SMILES: O=C1OC2(c3ccc(O)cc3Oc3cc(O)ccc32)c2ccc(NC(=S)NCCCCCn3ccnc3[N+](=O)[O-])cc21]

In some embodiments, the probe has the following structure, which is also referred to herein as HYPOX-2:

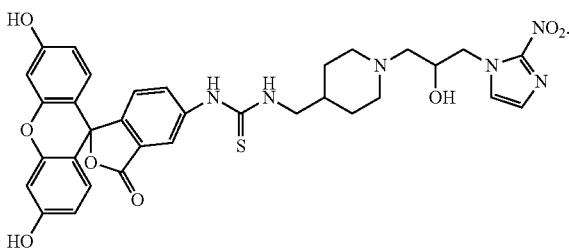 [SMILES: O=C1OC2(c3ccc(O)cc3Oc3cc(O)ccc32)c2ccc(NC(=S)NCC3CCN(CC(O)Cn4ccnc4[N+](=O)[O-])CC3)cc21]

Embodiments of the presently-disclosed probes are biocompatible. The term "biocompatible" as used herein describes a characteristic of compounds that do not typically induce undesirable or adverse side effects when administered in vivo. For example, biocompatible compounds may not induce side effects such as significant inflammation and/or acute rejection. It will be recognized that "biocompatibility" is a relative n, and some side effects can be expected even for some compounds that are biocompatible. In some embodiments, a biocompatible compound does not induce irreversible side effects, and in some embodiments a compound is biocompatible if it does not induce long term side effects. One test to determine biocompatibility is to measure whether cells die upon being exposed a composition in vitro. For instance, a biocompatible compound may cause less than about 30%, 20%, 10%, or 5% cell death.

Without being bound by theory or mechanism, embodiments of the probes disclosed acquire fluorescence as the nitro groups of the probe are bioreduced by nitroreductases in hypoxic cells or tissue ($pO_2$<10 mm Hg), triggering formation of intracellular protein adducts (16). In this regard, increasing fluorescent intensity is indicative of hypoxia. Distinctly, in other known systems for detecting hypoxia, the detection is carried out via antibody based immunohistochemical staining on excised tissues. The present probes and methods therefore represent a novel synthetic route to conjugate fluorescent dyes to nitroimidazoles towards enabling longitudinal in vivo imaging methods which facilitate imaging of hypoxic tissue while obviating the tissue dissection and processing steps.

The presently-disclosed subject matter also includes methods for imaging hypoxic cells and tissues of or in a subject. In some embodiments, the method involves contacting the cells or tissue with a probe as described herein, and detecting fluorescent intensity of the cell or tissue, wherein increased fluorescent intensity indicates that the cells or tissue is hypoxic. As will be appreciated by those of ordinary skill in the art, various techniques and systems can be used to detect fluorescent intensity and can be selected based on the particular context in which the method disclosed herein is being performed.

In some embodiments the method for imaging hypoxic cells and tissues include administering the present compounds to a subject, and then observing the activity of the probes in the proximity of the cells and tissues. In some embodiments the present imaging probes enable detection of hypoxia in cells or tissues via FRET or nitroreductase bioreduction mechanisms.

As will be recognized by those of ordinary skill in the art, the ability to image hypoxia in a variety of cells and tissue has particular advantages, including, for example, tumor cells or tissue, retinal cells or tissue, or other cells or tissue. By way of example, imaging tumor hypoxia can allow for better prognosis, for better determination of therapies for determining efficacy of certain treatments, e.g., radiation therapy, or for more effectively treating a cancer, e.g., identifying tumors or populations of cancerous cells that could be treated using anti-hypoxia therapies. For another example, imaging hypoxia associated with retinal cells can provide useful information about retinal disease.

The presently-disclosed methods are inclusive of research and cell-culture-based detection methods, as well as in vivo detection methods. Some embodiments of the methods disclosed herein involve administering the probe to living cells or tissue, or administering the probe in vivo, or administering the probe to a subject.

In some embodiments, the cells or tissue include retinal cells of a subject. Accordingly, the present probes and methods can be utilized for ophthalmic applications. Thus, this approach may be useful for diagnosing and/or prognosing hypoxia in the retina, which can further be utilized to diagnose and/or prognose retinal diseases or other diseases in other tissues featuring a hypoxic component. Thus, in some embodiments the method also involves identifying the subject as having hypoxic cells or tissue when there is increased fluorescent intensity detected. In some embodiments, the subject can be identified has having a retinal disease when there is increased fluorescent intensity detected.

In some embodiments, the cells or tissue include tumor cells of a subject, and the method also involves identifying the subject as having hypoxic cells or tissue when there is increased fluorescent intensity detected. In some embodiments, the method also involves determining a prognosis based on the detected fluorescent intensity. In some embodiments, the method also involves determining efficacy of a treatment based on the detected fluorescent intensity. In some embodiments, the method also involves recommending a treatment based on the detected fluorescent intensity, such as, for example, an anti-hypoxia treatment.

The terms "diagnosing" and "diagnosis" as used herein refer to methods by which the skilled artisan can estimate and even determine whether or not a subject is suffering from a given disease or condition. Along with diagnosis, clinical "prognosis" or "prognosticating" is also an area of great concern and interest. It is important to know the relative risk associated with particular conditions in order to plan the most effective therapy. If an accurate prognosis can be made, appropriate therapy, and in some instances less severe therapy or more effective therapy, for the patient can be chosen. In some embodiments of the presently disclosed subject matter, a method includes identifying a subject as having an increased risk of an eye or retinal disease, such as, but not limited to, diabetic retinopathy, retinopathy of prematurity, age-related macular degeneration, and the like.

The term "subject" as used herein refers to any target for the present probes. In some embodiments the subject can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The term "subject" includes human and veterinary subjects.

Additionally, the presently-disclosed subject matter includes methods for synthesizing the present probes.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

The presently-disclosed subject matter is further illustrated by the following specific but non-limiting examples. The following examples may include compilations of data that are representative of data gathered at various times during the course of development and experimentation related to the present invention.

EXAMPLES

Example 1

This Example describes methods and materials for studying embodiments of the presently-disclosed probes.

Human Müller Cells were a gift of Dr. John Penn (Vanderbilt Eye Institute, Nashville, Tenn.) and were purified and characterized as previously published (19). R28 rat retinal neuronal cells (18) were purchased from KeraFast. Low glucose DMEM, Fetal Bovine Serum and GlutaMax and Penicillin-Streptomycin were obtained from GIBCO. BrdU Cell Proliferation assay kit was obtained from Exalpha Biologicals. A Billups-Rothenberg chamber was used for hypoxia induction. Hypoxyprobe antibody was purchased from Hypoxyprobe Inc. Alexa Fluor 647 (AF647) secondary donkey anti-rabbit antibody and Prolong Gold mounting media with DAPI were purchased from Life Technologies.

C57BL6/J timed pregnant females were purchased from Charles River Laboratories. All animal experiments were approved by the Vanderbilt University Institutional Animal Care and Use Committee (IACUC).

Primary human Müller cells and R28 cell line were grown in low glucose DMEM supplemented with 10% Fetal Bovine Serum, 1× GlutaMAX, and 1× Penicillin-Streptomycin. All cells were maintained in a humidified environment with 5% $CO_2$ at 37° C. unless otherwise noted. For hypoxia induction, assay plates were placed into a humidified chamber and ambient air was displaced with a mixture of 5% $CO_2$ and 95% N2 at a flow rate of 20 L/min for 5 min according to manufacturer instructions and published methods (28). The chamber was clamped and placed at 37° C. for the remainder of the time point. R28 cells were treated with 100 μM pimonidazole hydrochloride diluted in complete media and subjected to hypoxia or normoxia for 4 h.

To perform in vitro imaging agent uptake assays, R28 cells or primary human Müller cells were seeded at a density of 15,000 cells per well in a 96-well black plate with clear bottom. When 90% confluent, assay plates were either place in hypoxia or kept in normoxia for 12 h. They were treated with imaging agents diluted in complete media and returned to hypoxia or kept in normoxia for 30 min. They were washed 4 times with pre-warmed Hank's Buffered Salt Solution (HBSS), kept in normoxia for 1 h, then washed 4 more times in HBSS. Fluorescence intensity was read (Absorbance: 490 nm, Emission: 520 nm) using a Synergy Mx Plate Reader from Biotek.

Immunofluorescence analysis of cells was performed by seeding R28 cells at a density of 15,000 cells per well of 8-well chamber slides. When 90% confluent, cells were treated with either imaging agent and pimonidazole hydrochloride or imaging agent only, diluted in complete media, and placed in hypoxia or normoxia for 4 h. Cells were washed 4 times in HBSS, fixed for 10 min with 10% neutral buffered formalin at room temperature, washed 3 times with tris buffered saline and mounted with Prolong Gold with DAPI mounting media.

For in vitro toxicity studies, a BrdU cell proliferation assay was performed on R28 cells. The assay was performed according to the manufacturer's protocol with the following specifications. Cells were seeded at 2000 cells/well in a 96-well plate. 24 h after seeding, the cells were serum starved for 6 h. Imaging agents and vehicle controls diluted in complete media were added and allowed to incubate for 24 h. 4 h prior to the end of the incubation, BrdU was added at a concentration of 10 μM.

The mouse model of oxygen induced retinopathy (OIR) was selected as a mouse model for hypoxia and generated as published (24). Briefly, litters with 6 to 8 pups were placed into a 75% oxygen chamber with dams from P7-P12. On P12, pups were removed from the hyperoxic environment to room air. Imaging agents, vehicle controls and dye controls were intravitreally injected (3 μg in 1 μL injection volume) or intravenously injected via tail vein (60 mg/kg) 6 h after removal from hyperoxic environment. Pimonidazole hydrochloride (Hypoxyprobe Inc.) was injected intraperitoneally at a concentration of 60 mg/kg body weight.

Immunofluorescence analysis of retinal tissues was performed by dissecting retinas from ocular tissues and fixing them in 10% neutral buffered formalin for 2 h. Tissues were then rinsed in Tris buffered saline and blocked/permeabilized in 10% donkey serum with 1% Triton X-100/0.05% Tween 20 in TBS for 6 h. Retinas were then stained for ICAM-2 and Hypoxyprobe followed by secondary antibody staining as indicated.

Example 2

Figure 1B:
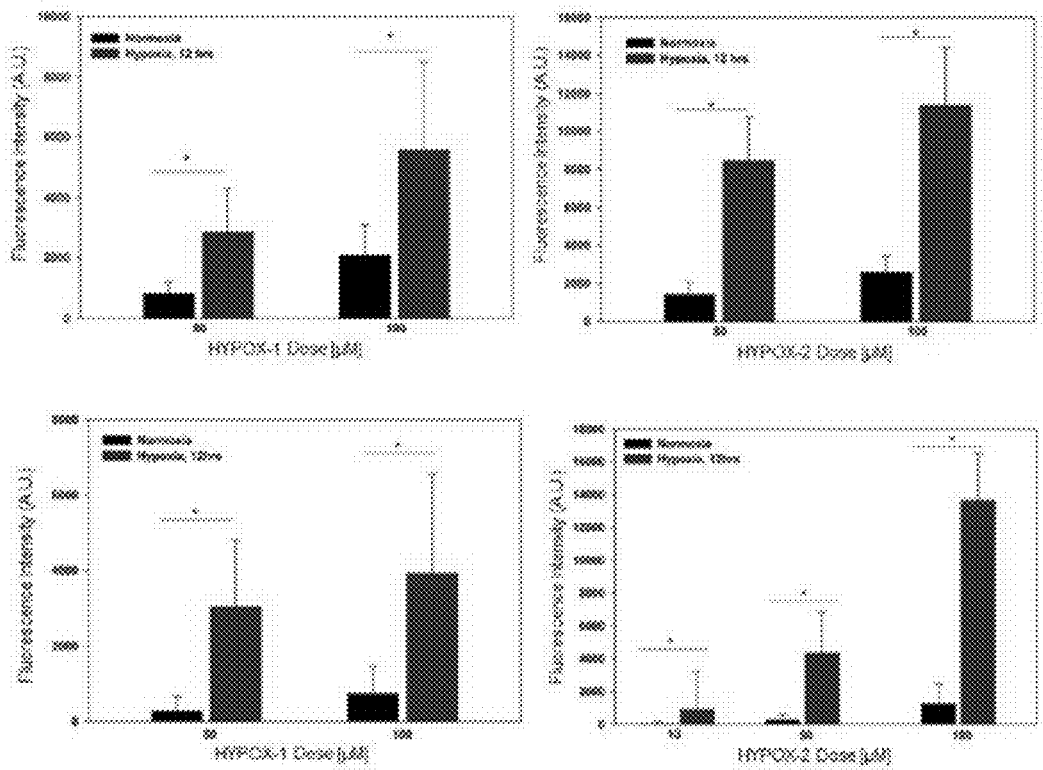
FIG. 1B. Hypoxic R28 and Müller cells treated with HYPOX imaging agents exhibit dose-dependent fluorescence enhancement in a microplate fluorescence spectrophotometric assay. Cells were conditioned under normoxic conditions or 12 h of hypoxia. (Upper Left Panel) HYPOX-1 treated R28 cell assay. (Upper Right Panel) HYPOX-2 treated R28 cell assay. (Lower Left Panel) HYPOX-1 treated Müller cell assay (Lower Right Panel) HYPOX-2 treated Müller cell assay. (n=8) * p<0.01.

In order to measure the specificity of HYPOX-1 and HYPOX-2 for hypoxic retinal tissues in vitro, R28 rat retinal neuronal (17, 18) or primary human Müller cells (19) were conditioned in a hypoxic chamber purged with a mixture of nitrogen/carbon dioxide up to 12 h. These two cell lines model predominant oxygen-sensitive cell types in retinal diseases with a hypoxia-ischemia component (20). Hypoxia was achieved in retinal cell lines, and was confirmed using qRT-PCR and Hypoxyprobe immunostaining (FIG. 1A). In a microplate fluorescence spectrophotometric assay (FIG. 1B), hypoxia-conditioned R28 cells and human Müller cells exhibited significantly higher fluorescence intensity than normoxia-conditioned R28 cells and human Müller cells when treated with HYPOX-1 and HYPOX-2. The micromolar doses of HYPOX-1 and HYPOX-2 used in these experiments are modeled on doses used to achieve optimal signal to background ratios using pimonidazole immunohistochemistry (21). At the concentration of piminidazole typically used for immunohistochemical assays (100 μM) HYPOX-1 and HYPOX-2 showed 5-fold and 11-fold increases in hypoxic/normoxic fluorescence intensity ratios in human Müller cells, respectively. At concentrations lower than 50 μM, HYPOX-1 was not detectable, however HYPOX-2 was effective at 10 μM in human Müller cells showing a 32-fold greater fluorescence intensity in hypoxia-conditioned cells. These data demonstrate that HYPOX-1 and -2 are selectively retained in hypoxic retinal cells irrespective of cell type and species origin.

Imaging of R28 cells incubated with the hypoxia-sensitive imaging agents further confirmed specificity and mechanism of action. As demonstrated by representative data shown in FIG. 2A-2F, HYPOX-2 accumulated in hypoxic cells but not normoxic cells to an appreciable degree. Furthermore, hypoxic cells incubated with HYPOX-2, but not normoxic cells, were positive for pimonidazole adducts as detectable by an adduct-specific antibody which does not bind to pimonidazole moieties alone (FIG. 2F). These results were further confirmed by Western Blot analysis (FIG. 2G), in which hypoxic and normoxic cell lysates were probed with a Hypoxyprobe antibody. These data suggest that HYPOX-1 and -2 accumulate in hypoxic cells by the same bioreduction/adduct formation mechanism observed for nitroimidazole compounds.

Figures 3A, 3B:
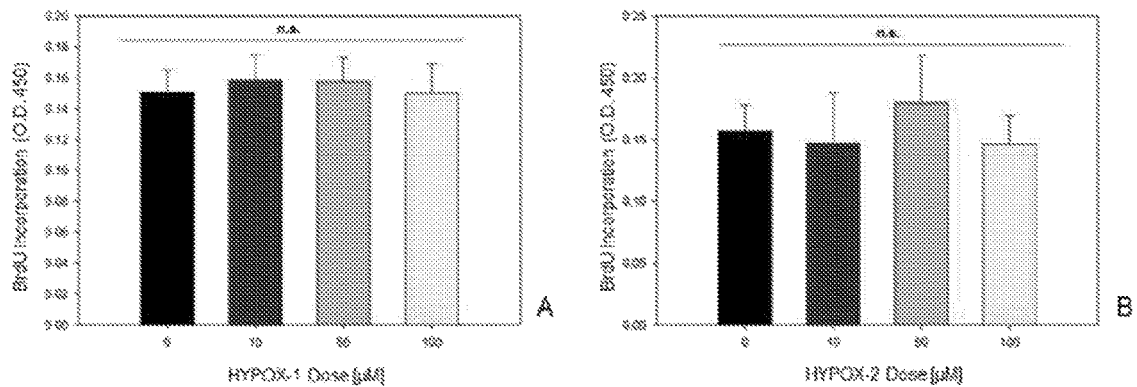
FIG. 3A-3B. R28 cells treated with (A) HYPOX-1 or (B) HYPOX-2 for 24 h show no significant decrease in cell proliferation as indicated by a BrdU incorporation assay. (n=4), p<0.01.

Both imaging agents were not acutely toxic to retinal cells as assessed by BrdU cell proliferation assays (FIG. 3). Cells exposed to up to 100 μM of HYPOX-1 or HYPOX-2 showed no significant decrease in cell proliferation indicating that these agents do not interfere with cell cycle and are safe at these concentrations. These data confirm the safety of the HYPOX components, fluorescein and nitroimidazoles.

Figures 4A, 4B, 4C, 4D, 4E, 4F:
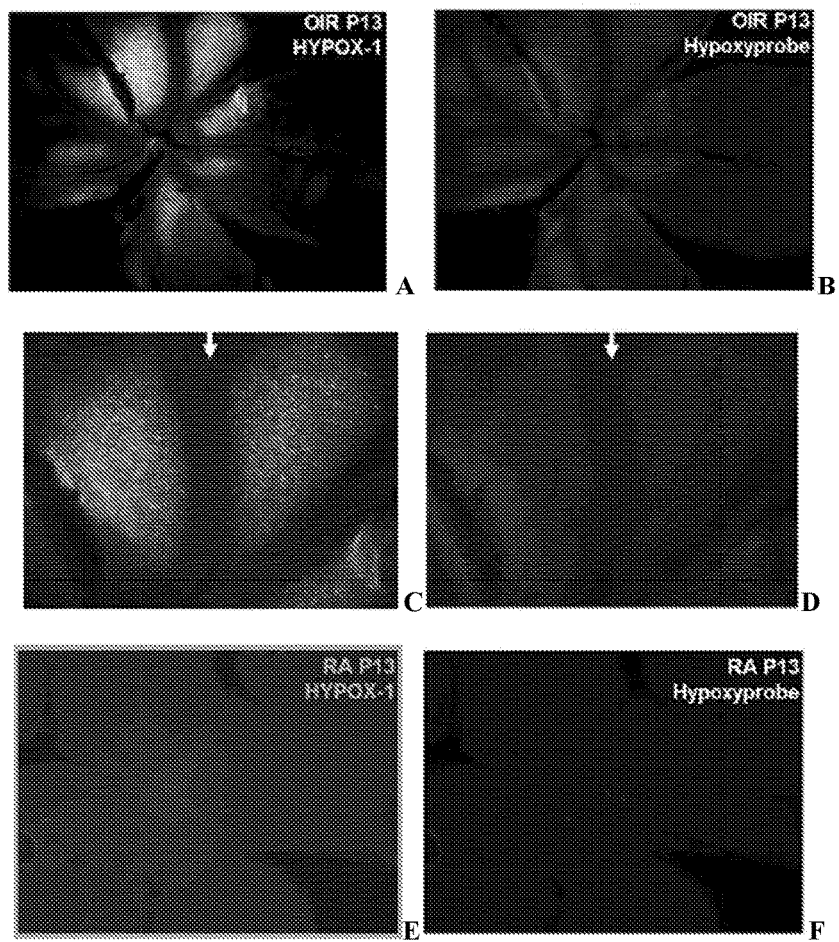
FIG. 4A-4F. Retinal flatmounts of the OIR model, which features avascular hypoxic retina, exhibit colocalization of intraocularly HYPOX-1 and pimonidazole.
Figure 5:
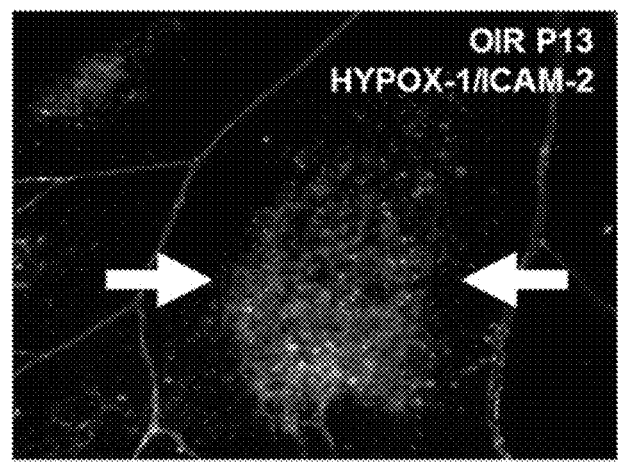
FIG. 5. Retinal flatmounts from OIR mice intravenously injected with HYPOX-1 (green) were stained with endothelial cell marker, ICAM-2 (red). Accumulation of HYPOX-1 is observed in avascular retina.

In order to demonstrate the in vivo hypoxia selectivity of these imaging agents in the retina, HYPOX-1 and HYPOX-2 were administered to mouse models of oxygen-induced retinopathy (OIR), which develop avascular, hypoxic central retinas on P13 and are used to model ischemic retinopathies observed in patients (24). Representative ex vivo imaging of dissected retinal flatmounts from OIR mice exhibited accumulation of intraocularly-injected HYPOX-1 in central avascular retinas which are hypoxic in these animals, as confirmed by positive immunostaining for pimonidazole hydrochloride (Hypoxyprobe) in the same region FIG. 4A-4E). HYPOX-1 did not accumulate in age matched control mice, which develop fully vascularized retinas (FIG. 4E). Staining of excised retinas with ICAM-2 was used to identify retinal vasculature and its association with HYPOX staining. As expected, intravenously-injected HYPOX-1 accumulated in avascular regions not supplied by the ICAM-2 positive blood vessels (FIG. 5). These data demonstrate the specificity of HYPOX probes for hypoxic tissue in vivo, and warrant further applications involving in vivo retinal imaging instrumentation. In addition, HYPOX accumulation in retinal tissue can be accomplished through intraocular or intravenous injection routes.

Figure 6:
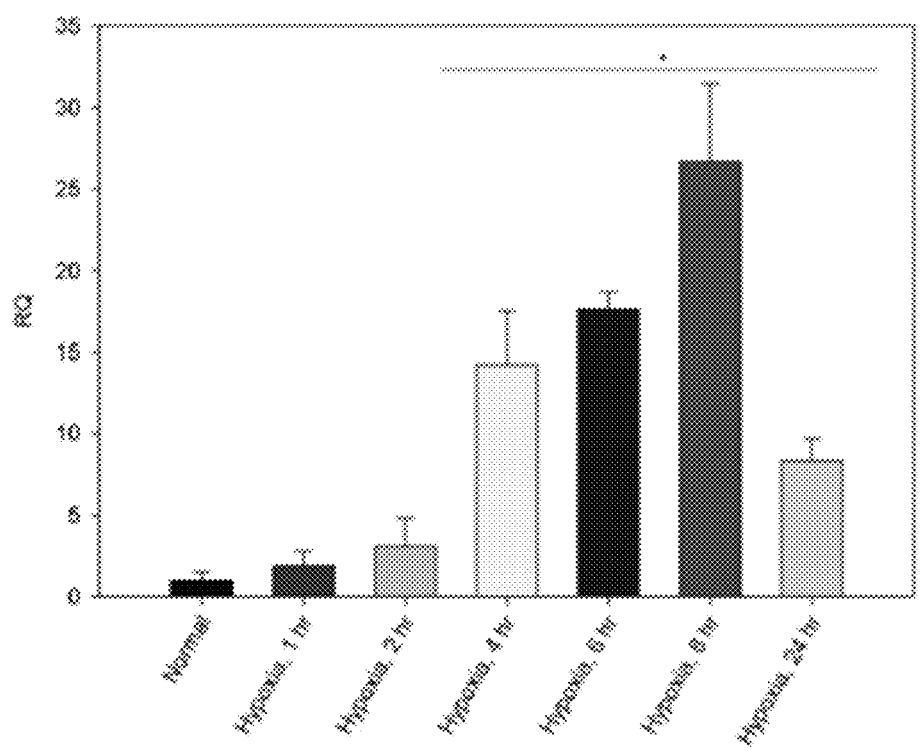
FIG. 6. Hypoxia-conditioned human retinal microvascular endothelial cells (HRMEC) for varying time points showed increased Carbonic Anhydrase II mRNA expression. (n=3, normalization to GUSB). * p<0.01

Additional studies were performed in hypoxia-conditioned human retinal microvascular endothelial cells (HRMEC) for varying time points, which showed increased Carbonic Anhydrase II mRNA expression (FIG. 6).

Example 3

This Example describes methods and materials for synthesizing embodiments of the presently-disclosed probes. Synthesis of HYPOX-1 was carried out according to methods described in herein, and was characterized using NMR and LC/MS analysis. HYPOX-1 features a 2-Nitroimidazole group coupled to FITC via a 6 carbon linkage. Similarly, synthesis and characterization of HYPOX-2 was carried out to yield a FITC dye attached directly to amine-activated pimonidazole.

The following includes details regarding synthesis of probes according to the presently disclosed subject matter.

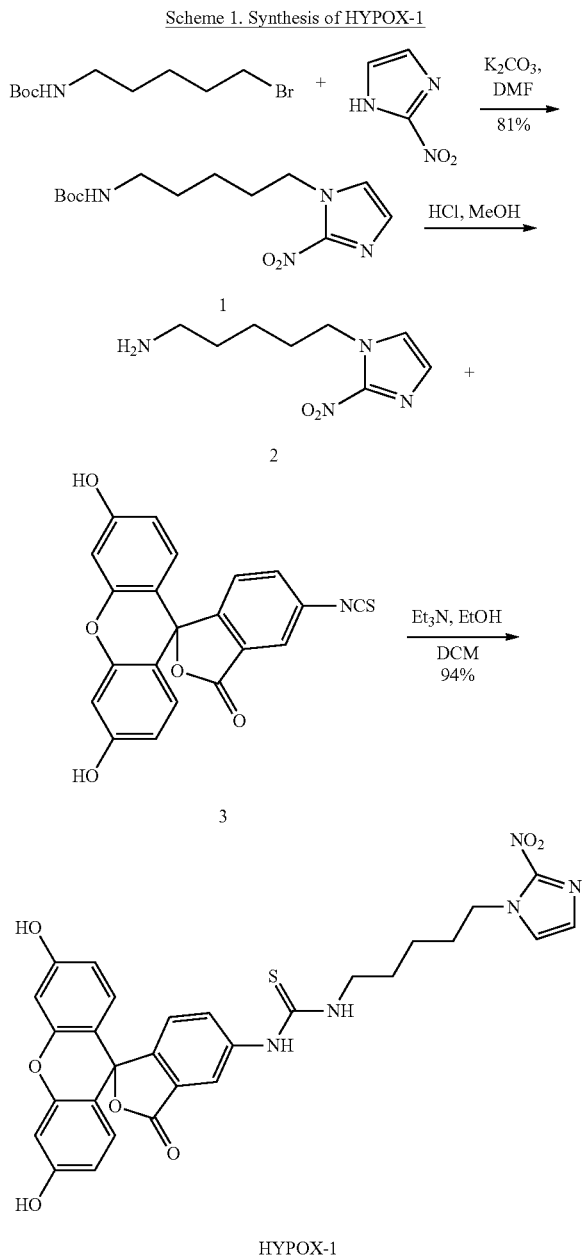

Scheme 1. Synthesis of HYPOX-1 tert-butyl (6-(2-nitro-1H-imidazol-1-yl)pentyl)carbamate 1

To a solution of 2-nitroimidazole (51 mg, 0.45 mmol) and tert-butyl (5-bromopentyl)carbainate (100 mg, 0.38 mmol) in DMF (3.5 mL) was added potassium carbonate (79 mg, 0.57 mmol). The reaction mixture was heated at 80° C. for 20 min under microwave then cooled to room temperature, filtered through a Celite pad and the filtrate concentrated in vacuo. The residue was purified by column chromatography using Hex/EtOAc (gradient: 0 to 50% EtOAc) to afford tert-butyl (5-(2-nitro-1H-imidazol-1-yl)pentyl)carbamate 1 (92 mg, 81%) as an oil. $^1$H NMR (CDCl$_3$, 400 MHz) δ (ppm) 7.14 (s, 1H), 7.08 (s, 1H), 4.41 (t, J=7.2 Hz, 2H), 3.14-3.10 (m, 2H), 1.88 (qt, J=7.6 Hz, 2H), 1.60-1.48 (m, 2H), 1.44 (s, 9H), 1.40-1.31 (m, 2H); LCMS (ES1) tR: 0.906 min (>99%, ELSD), m/z: 299.3 [M+1]+

5-(2-nitro-1H-imidazol-1-yl)pentan-1-amine 2

To a solution of compound 1, (143 mg, 0.48 mmol) in MeOH (5 mL) was added HCl (0.8 mL. 1.2 N solution) at room temperature. The reaction mixture was stirred for 5 h and solvent was removed in vacuo. The residue was washed with dichloromethane (3×20 mL) to afford 5-(2-nitro-tH-imidazol-1-yl)pentan-1-amine 2 (111 mg, 99%) as white solid. $^1$H NMR (MeOD, 400 MHz) δ ppm) 7.54 (s, 1H), 7.18 (s, 1H), 4.52 (t, J=7.2 Hz, 2H), 2.96 (t, J=7.6 Hz, 2H), 1.95 (qt, J=7.6 Hz, 2H), 1.74 (qt, J=7.6 Hz, 2H), 1.49 (qt, J=8.0 Hz, 2H); LCMS (ESI) tR: 0.082 min (>99%, ELSD), m/z: 284.16 [M+1]+

HYPOX-I.

To a solution of compound 2 (35 mg, 0.15 mmol) MeOH/dichloromethane (½ mL) was added triethylamine (42 µL, 0.3 mmol) followed by adding Fluorescein isothiocyanate 3 (58 mg, 0.15 mmol). The reaction mixture was heated at 80° C. for 15 min under microwave then cooled to room temperature and concentrated in vacuo. The residue was purified by column chromatography using dichloromethane/MeOH (gradient: 0 to 50% MeOH) to provide HYPOX-1 (55 mg, 64%) as yellow solid. $^1$H NAR (MeOD, 400 MHz) δ (ppm) 8.09 (d, J=1.6 Hz, 1H), 7.74 (d, J=8.0 Hz, 1H), 7.53 (d, J=0.8 Hz, 1H), 7.18 (d, J=8.4 Hz, 1H), 7.15 (d, J=0.8 Hz, 1H), 6.77 (d, J=8.8 Hz, 2H), 6.69 (d, J=2.4 Hz, 2H), 6.57 (dd, J=2.4, 8.4 Hz, 2H), 4.52 (t, J=7.2 Hz, 2H), 3.70-3.60 (m, 2H), 1.96 (qt, J=7.2 Hz, 2H), 1.74 (qt, J=7.2 Hz, 2H), 1.49 (qt, J=7.2 Hz, 2H); LCMS (ESI) tR: 0.756 min (>99%, ELSD), m/z: 673.1 [M+1]+

Figure 7:
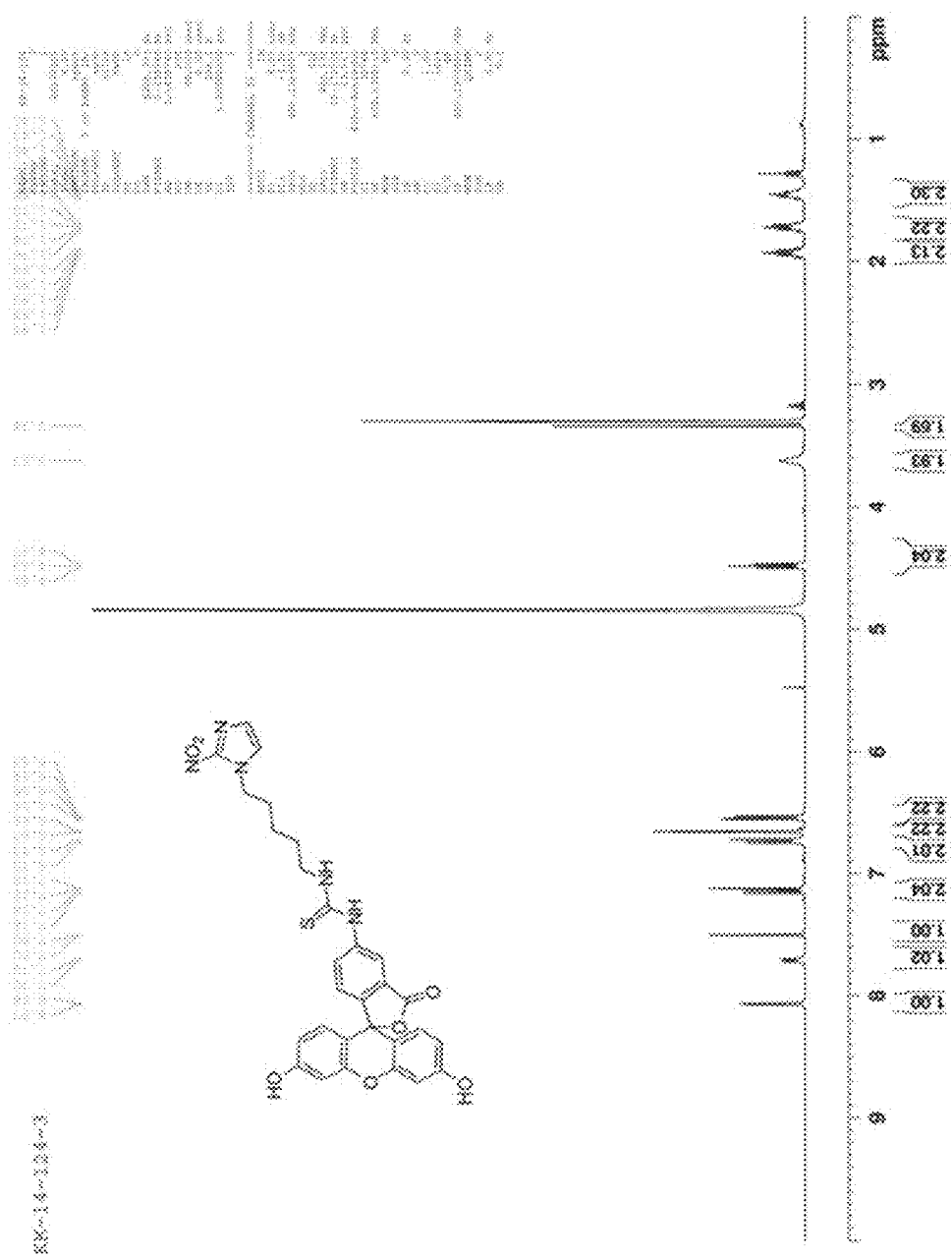
FIG. 7. $^1$H NMR spectra of HYPOX-1.
Figure 8:
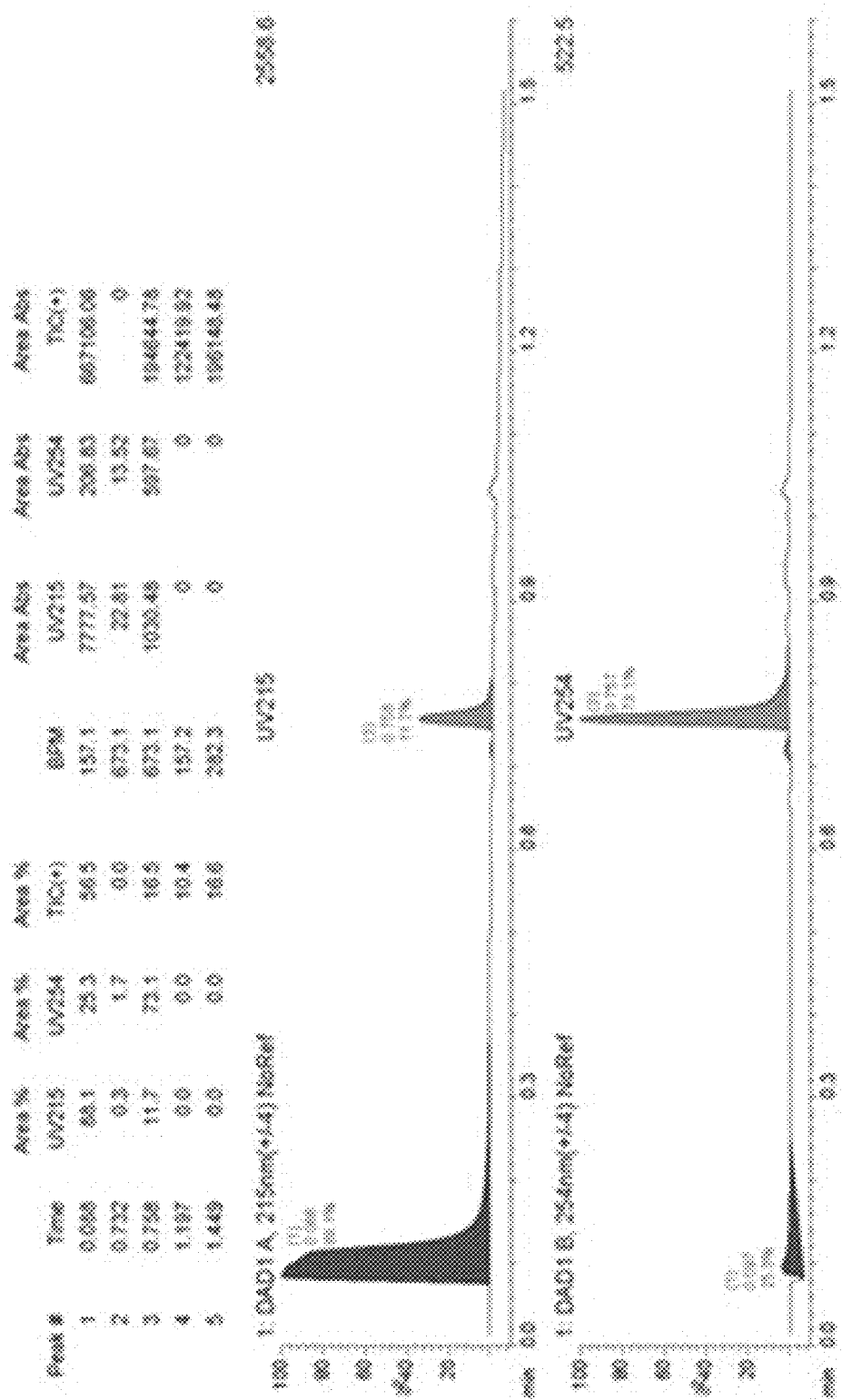
FIG. 8. HYPOX-1 LCMS (ESI) tR: 0.756 min (99%, ELSD), m/z: 673.1 $[M+1]^+$

Reference is also made to FIG. 7 ($^1$H NMR spectra of HYPOX-1) and FIG. 8 (HYPOX-1 LCMS (ESI) tR: 0.756 min (99%, ELSD), m/z: 673.1 [M+1]$^+$).

Scheme 2. Synthesis of HYPOX-2

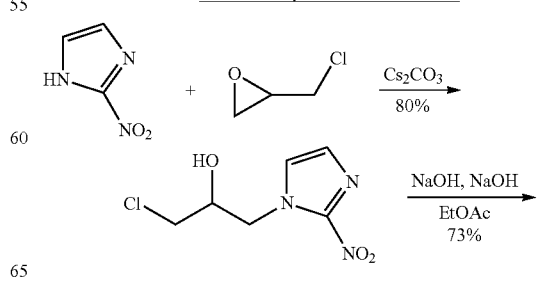

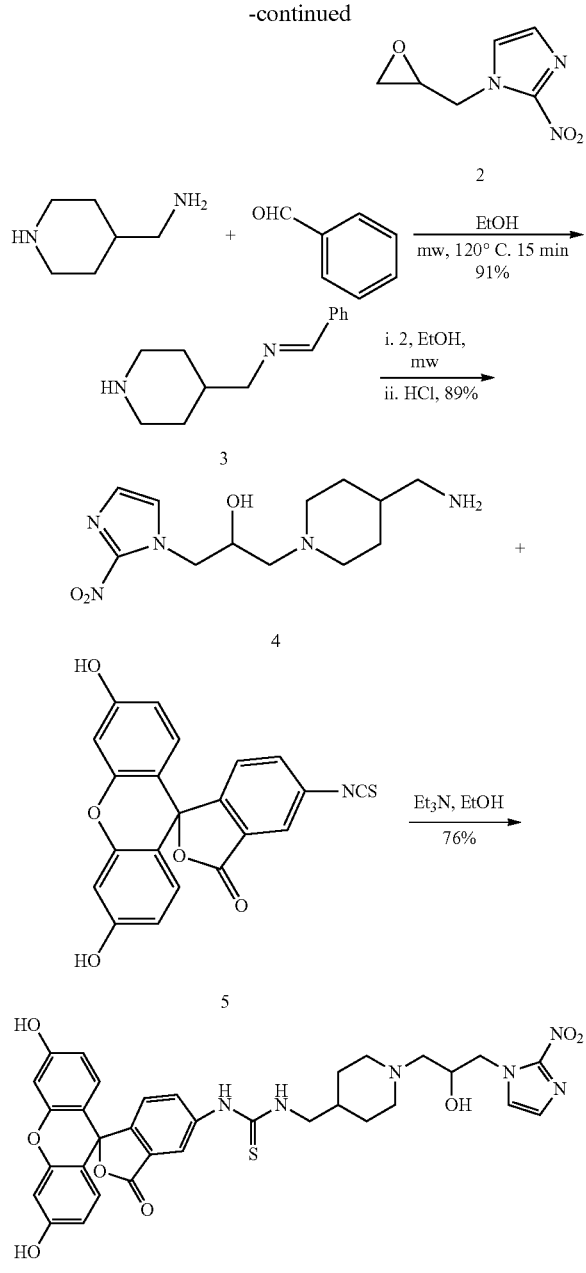

2-nitro-1-(oxiran-2-ylmethyl)-H-imidazole 2

A mixture of 2-nitroimidazole (250 mg, 2.21 mmol), epichlorohydrin (5 mL) and potassium carbonate (31 mg, 0.22 mmol) was heated under reflux condition for 20 min. The yellow 1-chloro-3-(2-nitro-1H-imidazol-1-yl)propan-2-ol 1 was collected by filtration and then dissolved in mixture of ethylacetate (5 mL) and sodium hydroxide (5 mL, 2 M solution). The reaction mixture was stirred for 1 h at room temperature and extracted with ethylacetate (3×5 mL) then the organic layer was dried over MgSO$_4$. The residue was purified by column chromatography using dichloromethane/MeOH (gradient: 0 to 10% MeOH) to provide white solid 2-nitro-1-(oxiran-2-ylmethyl)-1H-imidazole 2. (300 mg, 66%).

(E)-N-benzylidene-1-(piperidin-4-yl)methanamine 3

A mixture of piperidin-4-ylmethanamine (1.48 mL, 12.3 mmol) and benzaldehyde (1.28 mL, 12.3 mmol) in ethanol (9.4 mL) was heated at 120° C. for 15 min under microwave condition then solvent was removed in vacuo to give (E)-N-benzylidene-1-(piperidin-4-yl)methanamine 3 as a yellow oil (2.71 g, 91%) and used without further purification.

1-(4-(aminomethyl)piperidin-1-yl)-3-(2-nitro-1H-imidazol-1-yl)propan-2-ol 4

A mixture of (E)-N-benzylidene-1-(piperidin-4-yl)methanamine 3 (310 mg, 1.54 mmol) and 2-nitro-1-(oxiran-2-ylmethyl)-1H-imidazole 2 (217 mg, 1.28 mmol) in ethanol (8 mL) was heated at 120° C. for 20 min under microwave condition then concentrated under reduced pressure. 2 mL of HCl (1.2 N solution) was added to the resulting residue, then the mixture was heated at 40° C. for 4 h. The reaction mixture was extracted with dichloromethane (4×8 mL). The aqueous layer was treated with 40% of NaOH solution to adjust pH 11 then extracted with dichloromethane (4×10 mL) to provide 4 as yellow oil (325 mg, 89%). $^1$NMR (MeOD, 400 MHz) δ (ppm) 7.47 (s, 1H), 7.14 (s, 1H), 4.78 (dd, J=14.0, 2.0 Hz, 1H), 4.30 (dd, J=14.0, 8.0 Hz, 1H), 4.15-4.10 (m, 1H), 3.00 (d, J=11.2 Hz, 1H), 2.91 (d, J=11.2 Hz, 1H), 2.52 (d, J=6.4 Hz, 2H), 2.48-2.35 (m, 2H), 2.05 (dd, J=24.0, 11.6 Hz, 2H), 1.74 (d, J=11.2 Hz, 2H), 1.42-1.22 (m, 3H)); LCMS (ESI) tR: 0.901 min (>99%, ELSD), m/z: 588.1 [M+1]+

HYPOX-2.

To a solution of 4 (27 mg, 0.095 mmol) in mixture of ethanol/dichloromethane (½ mL) was added triethylamine (26 µL, 0.19 mmol), followed by adding Fluorescein isothiocyanate 5 (37 mg, 0.095 mmol). The reaction mixture was heated at 80° C. for 15 min under microwave then cooled to room temperature and concentrated in vacuo. The residue was purified by column chromatography using dichloromethane/MeOH (gradient: 0 to 50% MeOH) to provide HYPOX-2 (49 mg, 76%) as yellow solid. $^1$H NMR (DMSO, 400 MHz) δ (ppm) 8.13 (bs, 1H), 7.72 (d, J=8.0 Hz, 1H), 7.55 (s, 1H), 7.16 (d, J=8.0 Hz, 1H), 7.13 (s, 1H), 6.66 (d, J=2.0 Hz, 2H), 6.60-6.52 (m, 4H), 4.67 (dd, J=14.0, 3.2 Hz, 1H), 4.20 (dd, J=14.0, 8.0 Hz, 1H), 4.10-3.95 (m, 1H), 3.42-3.38 (m, 2H), 2.90 (d, J=10.4 Hz, 1H), 2.77 (d, J=10.4 Hz, 1H), 2.32-2.20 (m, 2H), 1.99-1.83 (m, 2H), 1.70-1.62 (m, 2H), 1.23-1.01 (m, 3H)); LCMS (ESI) tR: 0.901 min (>99%, ELSD), m/z: 588.1 [M+1]1+

Figure 9:
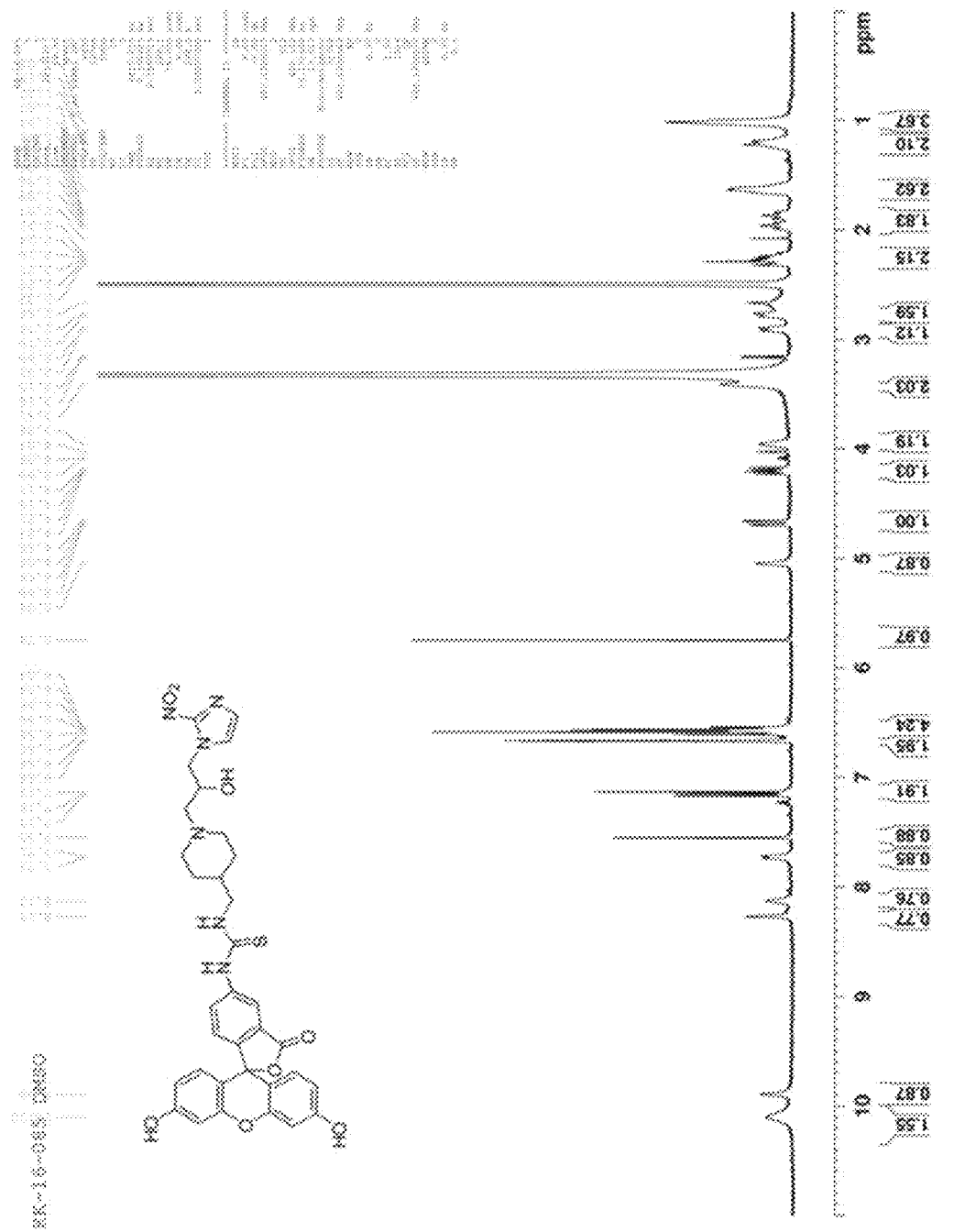
FIG. 9. $^1$H NMR spectra of HYPOX-2.
Figure 10:
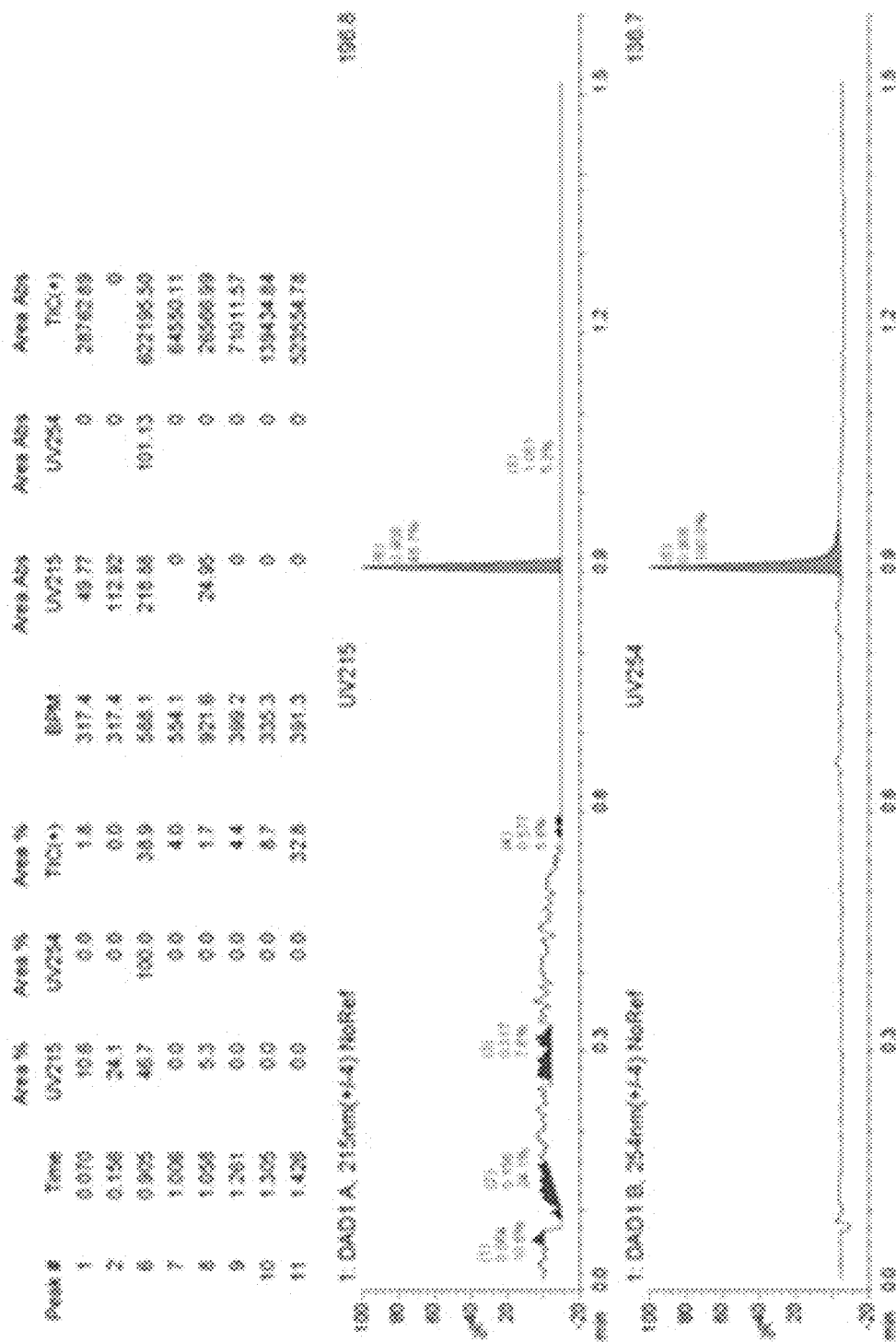
FIG. 10. HYPOX-2 LCMS (ESI) tR: 0.901 min (99%, ELSD), m/z: 588.1 $[M+1]^+$

Reference is also made to FIG. 9 ($^1$H NMR spectra of HYPOX-2) and FIG. 10 (HYPOX-2 LCMS (ESI) tR: 0.901 min (99%, ELSD), m/z: 588.1 [M+1]$^+$).

Throughout this document, various references are mentioned. All such references are incorporated herein by reference, including the references set forth in the following list:

REFERENCES

1. Cunha-Vaz, J. G. (2004) The blood-retinal barriers system. Basic concepts and clinical evaluation. *Experimental eye research* 78, 715-21.
2. Linsenmeier, R. A., Braun, R. D., McRipley, M. A., Padnick, L. B., Ahmed, J., Hatchell, D. L., McLeod, D. S., and Lutty, G. A. (1998) Retinal hypoxia in long-term diabetic cats. *Investigative ophthalmology & visual science* 39, 1647-57.

3. Poulaki, V., Qin, W., Joussen, A. M., Hurlbut, P., Wiegand, S. J., Rudge, J., Yancopoulos, G. D., and Adamis, A. P. (2002) Acute intensive insulin therapy exacerbates diabetic blood-retinal barrier breakdown via hypoxia-inducible factor-1alpha and VEGF. *The Journal of clinical investigation* 109, 805-15.

4. Grunwald, J. E., Metelitsina, T. I., Dupont, J. C., Ying, G. S., and Maguire, M. G. (2005) Reduced foveolar choroidal blood flow in eyes with increasing AMD severity. *Investigative ophthalmology & visual science* 46, 1033-8.

5. Metelitsina, T. I., Grunwald, J. E., DuPont, J. C., and Ying, G. S. (2006) Effect of systemic hypertension on foveolar choroidal blood flow in age related macular degeneration. *The British journal of ophthalmology* 90, 342-6.

6. Traustason, S., Kiilgaard, J. F., Karlsson, R. A., Hardarson, S. H., Stefansson, E., and la Cour, M. (2013) Spectrophotometric retinal oximetry in pigs. *Investigative ophthalmology & visual science* 54, 2746-51.

7. Hardarson, S. H., Elfarsson, A., Agnarsson, B. A., and Stefansson, E. (2013) Retinal oximetry in central retinal artery occlusion. *Acta ophthalmologica* 91, 189-90.

8. Hammer, M., Vilser, W., Riemer, T., and Schweitzer, D. (2008) Retinal vessel oximetry-calibration, compensation for vessel diameter and fundus pigmentation, and reproducibility. *Journal of biomedical optics* 13, 054015.

9. Hardarson, S. H., Harris, A., Karlsson, R. A., Halldorsson, G. H., Kagemann, L., Rechtman, E., Zoega, G. M., Eysteinsson, T., Benediktsson, J. A., Thorsteinsson, A., Jensen, P. K., Beach, J., and Stefansson, E. (2006) Automatic retinal oximetry. *Investigative ophthalmology & visual science* 47, 5011-6.

10. Kristjansdottir, J. V., Hardarson, S. H., Harvey, A. R., Olafsdottir, O. B., Eliasdottir, T. S., and Stefansson, E. (2013) Choroidal oximetry with a noninvasive spectrophotometric oximeter. *Investigative ophthalmology & visual science* 54, 3234-9.

11. Wanek, J., Teng, P. Y., Blair, N. P., and Shahidi, M. (2013) Inner retinal oxygen delivery and metabolism under normoxia and hypoxia in rat. *Investigative ophthalmology & visual science* 54, 5012-9.

12. Dai, C., Liu, X., Zhang, H. F., Puliafito, C. A., and Jiao, S. (2013) Absolute retinal blood flow measurement with a dual-beam Doppler optical coherence tomography. *Investigative ophthalmology & visual science* 54, 7998-8003.

13. Ljungkvist, A. S., Bussink, J., Rijken, P. F., Raleigh, J. A., Denekamp, J., and Van Der Kogel, A. J. (2000) Changes in tumor hypoxia measured with a double hypoxic marker technique. *Int J Radiat Oncol Biol Phys* 48, 1529-38.

14. Varia, M. A., Calkins-Adams, D. P., Rinker, L. H., Kennedy, A. S., Novotny, D. B., Fowler, W. C., Jr., and Raleigh, J. A. (1998) Pimonidazole: a novel hypoxia marker for complementary study of tumor hypoxia and cell proliferation in cervical carcinoma. *Gynecologic oncology* 71, 270-7.

15. Arteel, G. E., Thurman, R. G., and Raleigh, J. A. (1998) Reductive metabolism of the hypoxia marker pimonidazole is regulated by oxygen tension independent of the pyridine nucleotide redox state. *European journal of biochemistry/FEBS* 253, 743-50.

16. Nordsmark, M., Loncaster, J., Aquino-Parsons, C., Chou, S. C., Ladekarl, M., Haysteen, H., Lindegaard, J. C., Davidson, S. E., Varia, M., West, C., Hunter, R., Overgaard, J., and Raleigh, J. A. (2003) Measurements of hypoxia using pimonidazole and polarographic oxygen-sensitive electrodes in human cervix carcinomas. *Radiotherapy and oncology: journal of the European Society for Therapeutic Radiology and Oncology* 67, 35-44.

17. Seigel, G. M. (1996) Establishment of an E1A-immortalized retinal cell culture. *In vitro cellular & developmental biology. Animal* 32, 66-8.

18. Seigel, G. M., Mutchler, A. L., Adamus, G., and Imperato-Kalmar, E. L. (1997) Recoverin expression in the R28 retinal precursor cell line. *In vitro cellular & developmental biology. Animal* 33, 499-502.

19. Capozzi, M. E., McCollum, G. W., and Penn, J. S. (2014) The role of cytochrome P450 epoxygenases in retinal angiogenesis. *Investigative ophthalmology & visual science* 55, 4253-60.

20. Penn, J. S., Madan, A., Caldwell, R. B., Bartoli, M., Caldwell, R. W., and Hartnett, M. E. (2008) Vascular endothelial growth factor in eye disease. *Progress in retinal and eye research* 27, 33171.

21. Yaromina, A., Zips, D., Thames, H. D., Eicheler, W., Krause, M., Rosner, A., Haase, M., Petersen, C., Raleigh, J. A., Quennet, V., Walenta, S., Mueller-Klieser, W., and Baumann, M. (2006) Pimonidazole labelling and response to fractionated irradiation of five human squamous cell carcinoma (hSCC) lines in nude mice: the need for a multivariate approach in biomarker studies. *Radiotherapy and oncology: journal of the European Society for Therapeutic Radiology and Oncology* 81, 122-9.

22. Nordsmark, M., Loncaster, J., Chou, S. C., Haysteen, H., Lindegaard, J. C., Davidson, S. E., Varia, M., West, C., Hunter, R., Overgaard, J., and Raleigh, J. A. (2001) Invasive oxygen measurements and pimonidazole labeling in human cervix carcinoma. *International journal of radiation oncology, biology, physics* 49, 581-6.

23. Gass, J. D., Sever, R. J., Sparks, D., and Goren, J. (1967) A combined technique of fluorescein funduscopy and angiography of the eye. *Archives of ophthalmology* 78, 455-61.

24. Smith, L. E., Wesolowski, E., McLellan, A., Kostyk, S. K., D'Amato, R., Sullivan, R., and D'Amore, P. A. (1994) Oxygen-induced retinopathy in the mouse. *Invest Ophthalmol Vis Sci* 35, 101-11.

25. Piao, W., Tsuda, S., Tanaka, Y., Maeda, S., Liu, F., Takahashi, S., Kushida, Y., Komatsu, T., Ueno, T., Terai, T., Nakazawa, T., Uchiyama, M., Morokuma, K., Nagano, T., and Hanaoka, K. (2013) Development of azo-based fluorescent probes to detect different levels of hypoxia. *Angewandte Chemie* 52, 13028-32.

26. Kiyose, K., Hanaoka, K., Oushiki, D., Nakamura, T., Kajimura, M., Suematsu, M., Nishimatsu, H., Yamane, T., Terai, T., Hirata, Y., and Nagano, T. (2010) Hypoxia-sensitive fluorescent probes for in vivo real-time fluorescence imaging of acute ischemia. *Journal of the American Chemical Society* 132, 15846-8.

27. Takahashi, S., Piao, W., Matsumura, Y., Komatsu, T., Ueno, T., Terai, T., Kamachi, T., Kohno, M., Nagano, T., and Hanaoka, K. (2012) Reversible off-on fluorescence probe for hypoxia and imaging of hypoxia-normoxia cycles in live cells. *Journal of the American Chemical Society* 134, 19588-91.

Dai, Y., Bae, K., and Siemann, D. W. (2011) Impact of hypoxia on the metastatic potential of human prostate cancer cells. *International journal of radiation oncology, biology, physics* 81, 521-8.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A probe for detecting hypoxic cells and tissue, comprising:
a fluorescein moiety having the structure of

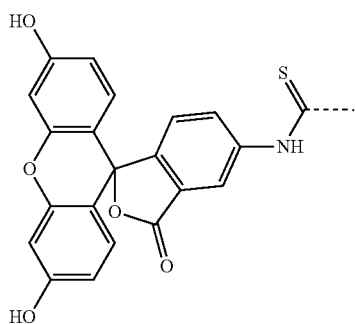

a nitroimidazole compound moiety, and
a linker conjugating the fluorescein moiety to the nitroimidazole compound moiety.

2. The probe of claim 1, wherein the nitroimidazole compound is selected from 2-nitroimidazole and pimonidazole.

3. The probe of claim 1, having the structure of

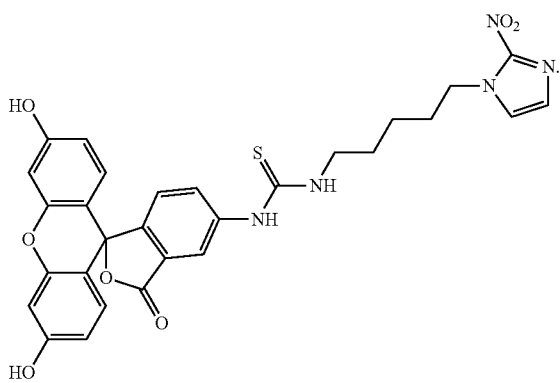 [SMILES: O=C1OC2(c3ccc(O)cc3Oc3cc(O)ccc32)c2ccc(NC(=S)NCCCCCn3ccnc3[N+](=O)[O-])cc21]

4. The probe of claim 1, having the structure of

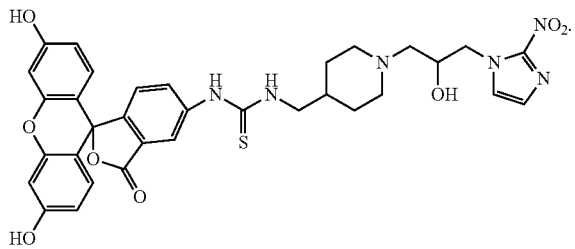 [SMILES: O=C1OC2(c3ccc(O)cc3Oc3cc(O)ccc32)c2ccc(NC(=S)NCC3CCN(CC(O)Cn4ccnc4[N+](=O)[O-])CC3)cc21]

5. A method for detecting hypoxic cells and tissue, comprising:
contacting the cells or tissue with the probe of claim 1; and
detecting fluorescent intensity of the cell or tissue, wherein increased fluorescent intensity indicates that the cells or tissue is hypoxic.

6. The method of claim 5, wherein the nitro groups of the probe are bioreduced by nitroreductases in hypoxic cells or tissue, thereby increasing fluorescent intensity.

7. The method of claim 5, wherein the cells or tissue include retinal cells.

8. The method of claim 5, wherein the cells or tissue include tumor cells.

9. The method of claim 5, wherein contacting the cell or tissue with the probe comprises administering the probe to living cells or tissue.

10. The method of claim 5, wherein the cells or tissue include retinal cells of a subject, and further comprising identifying the subject as having hypoxic cells or tissue when there is increased fluorescent intensity detected.

11. The method of claim 10, and further comprising identifying the subject as having a retinal disease when there is increased fluorescent intensity detected.

12. The method of claim 5, wherein the cells or tissue include tumor cells of a subject, and further comprising identifying the subject as having hypoxic cells or tissue when there is increased fluorescent intensity detected.

13. The method of claim 12, and further comprising determining a prognosis based on the detected fluorescent intensity.

14. The method of claim 12, and further comprising determining efficacy of a treatment based on the detected fluorescent intensity.

15. The method of claim 12, and further comprising recommending a treatment based on the detected fluorescent intensity.

* * * * *